United States Patent [19]
Cardillo et al.

[11] Patent Number: 4,950,607
[45] Date of Patent: Aug. 21, 1990

[54] PROCESS FOR THE MICROBIOLOGICAL PRODUCTION OF GAMMA (R) DECANOLIDE AND GAMMA (R) OCTANOLIDE

[75] Inventors: Rosanna Cardillo; Claudio Fuganti, both of Milan; Giuseppe Sacerdote, Turin; Massimo Barbeni, Turin; Paolo Cabella, Turin; Francesco Squarcia, Bologna, all of Italy

[73] Assignee: Pernod-Ricard, Paris, France

[21] Appl. No.: 388,674

[22] Filed: Aug. 2, 1989

[30] Foreign Application Priority Data

Aug. 4, 1988 [IT] Italy .............................. 67742 A/88

[51] Int. Cl.$^5$ .............................................. C12N 9/20
[52] U.S. Cl. .................................. 435/280; 435/148; 435/198; 435/254; 435/911; 435/938; 435/917
[58] Field of Search ............... 435/911, 148, 146, 132, 435/134, 198, 280

[56] References Cited

U.S. PATENT DOCUMENTS

| | | | |
|---|---|---|---|
| 3,076,750 | 11/1963 | Muys et al. | 435/136 |
| 3,562,112 | 2/1971 | Gibian et al. | 435/136 |
| 4,059,488 | 7/1977 | Hachikubo et al. | 435/134 |
| 4,204,044 | 3/1980 | Suhara et al. | 435/280 |
| 4,275,081 | 6/1981 | Coleman et al. | 435/134 |
| 4,560,656 | 3/1985 | Farbood et al. | 435/148 |

*Primary Examiner*—Ronald W. Griffin
*Assistant Examiner*—Pamela S. Webber
*Attorney, Agent, or Firm*—Dressler, Goldsmith, Shore, Sutker & Milnamow, Ltd.

[57] ABSTRACT

The process for the microbiological production of gamma (R) decanolide and/or gamma (R) octanolide involves the culture of a micro-organism selected from the group comprising *Aspergillus niger*, *Cladosporium suaveolens*, *Phanerochaete chrysosporium* and *Pichia etchellsii* in a culture medium that includes a vegetable oil, particularly castor oil, sunflower oil and coconut oil and their hydrolysates.

8 Claims, No Drawings

PROCESS FOR THE MICROBIOLOGICAL PRODUCTION OF GAMMA (R) DECANOLIDE AND GAMMA (R) OCTANOLIDE

The present invention relates to a process for the production by microbiological means of an optically active gamma-lactone, particularly the lactone of 4-hydroxydecanoic acid (4R) (gamma-decanolide or gamma decalactone) and the lactone of 4-hydroxyoctanoic acid (4R) (gamma-octanolide).

The lactones quoted above are volatile substances that are very important in practical terms as they are present in natural foodstuffs whose flavour they help to form.

It is not economical to extract these compounds from natural sources because of the small quantities in which they generally exist and because it is difficult physically to separate them from the other volatile compounds that are present with them.

U.S. Pat. No. US-A-4,560,656 describes a process for the production of gamma-decalactone which exploits the ability of some species of the Candida, Aspergillus, Geotrichum and Yarrovia genus oxidatively to degrade ricinoleic acid that is added to the culture in that form or in the form of castor oil, in the presence or absence of an external lipase, to give 4-hydroxydecanoic acid (4R) or the corresponding lactone directly.

The fact that gamma-hydroxydecanoic acid is an intermediate in the oxidative degradation of ricinoleic acid by strains belonging to the Candida genus has already been studied by Okui et al (J. Biochemistry, 54, 536–540, 1963).

U.S. Pat. No. US-A-4,396,715 describes a process for obtaining a flavouring comprising octa-, nona- and deca-lactones by incubating a micro-organism of the Pityrosporum genus.

The subject of the present invention is a process for the production of optically active gamma-decanolide and/or gamma-octanolide which involves bringing a vegetable oil, one of its hydrolysates and/or natural ricinoleic acid into contact with a growing culture of a micro-organism selected from the group comprising *Aspercillus niger* (CBS 102.12), *Cladosporium suaveolens* (CBS 157.58), *Pichia etchellsii* (CBS 2011) and *Phanerochaete chrysosporium* (CBS 57863).

In particular it is preferable to use castor oil, sunflower oil, their hydrolysates or ricinoleic acid to produce gamma-decanolide.

It is preferable to use coconut oil in contact with a growing culture of *Cladoscorium suaveolens* to produce gamma-octanolide. The use of sunflower oil represents a considerable economic advantage in the process according to the invention because it is inexpensive. A further advantage lies in the possibility of using natural ricinoleic acid which is sufficiently non-toxic to the microorganisms quoted above not to inhibit their metabolism. The use of ricinoleic acid has particular advantages in the separation phase of the required lactone because this is well known to be particularly simple in an acid medium.

The required lactone starts to be produced from the materials mentioned above in variable culture conditions and in a relatively short time, between 24 and 60 hours. Typically, the micro-organisms are kept in contact with the materials mentioned above at temperatures between 20 and 30° C. inclusive.

The nutrient medium in which the micro-organisms are grown is of the conventional type and in this respect reference should be made to the examples which follow. The culture takes place under agitation as regards the degradation phase in which the lactone is produced whilst production of the biomass used as the pre-inoculum may take place with or without agitation and may be monitored in respect of the production of the required compound by standard technical methods such as GLC, TLC, HPLC, IR and NMR. When analysis shows that production has reached a maximum the required lactone is extracted. As is known see the paper by I L Finar in Organic Chemistry Vol. I, pp. 427–428 for example) the lactone form of the required compound is subject to exchange with the corresponding gamma-hydroxyacid and the extraction of the lactone thus implies the transformation of the gamma-hydroxyacid into the corresponding lactone. (1) To extract the lactone the culture medium is filtered over Celite (R), washed with ethyl acetate and the aqueous phase, of acid pH, preferably pH 5, is extracted, preferably twice with ethyl acetate. The combined organic phases are extracted twice with a 5% potassium carbonate solution to remove the acidic portions. The organic phase, dried on sodium sulphate, is then evaporated and the residue distilled at 150° C. and 1-3 mm Hg to give gamma-decanolide or gamma-octanolide. (2) To improve the yield of lactone the γ hydroxy decanoic acid can be lactonized in the medium by bringing the pH between 1 and 5, preferably 1 and 3, by the addition of a suitable acid, and by heating the acidified medium at a temperature between 50° C. and 110° C., preferably between 90° and 100° C., for about between 10 mn and 2 h according to the temperature. The lactone can be stripped from the medium by water vapor from the acidified medium.

In the examples which follow the quantity of lactone produced is expressed as a percentage as obtained from GLC analysis.

EXAMPLE 1

A suspension of *Aspergillus niger* (CBS 102.12) is inoculated into a 300 ml Erlenmeyer flask containing a solution of 2% Merck nutrient, 0.02% Tween 80 and 5 g of ricinoleic acid pH 7 which has been sterilized in an autoclave for 10 minutes at 120° C.; this is kept at 27°–30° C. for between two and five days and is agitated throughout. Samples are taken during this period and the gamma decanolide in the organic extract which is obtained by whisking the sample with ethyl ether is determined by GLC. The gamma-decanolide content found is between 4 and 12%.

EXAMPLE 2

The procedure in Example 1 is repeated but with *Cladoscorium suaveolens* (CBS 157.58). The gamma decanolide content found is between 4 and 10%.

EXAMPLES 3 and 4

The procedures in Examples 1 and 2 are repeated but 6 g of castor oil are used instead of ricinoleic acid. Approx. 5% gamma decanolide is obtained in both cases after four days' incubation.

EXAMPLE 5

Separation Process

The procedures described in examples 1 and 2 are carried out with five Erlenmeyer flasks, using 25 g of ricinoleic acid in all; after 48 hours the cultures are filtered over Celite and the Celite washed with ethyl acetate.

The aqueous phase, pH 5, is extracted twice with ethyl acetate. The organic Celite extraction and washing phases (220 ml) are extracted twice with 150 ml of a 5% K2CO3 solution. The organic phase is dried over sodium sulphate and evaporated to dryness. TLC indicates the presence of gamma decanolide and much more mobile products (7 parts hexane eluent, 3 parts ethyl acetate). This substance is distilled in a balloon flask to give approx. 350 mg of gamma decanolide, 99.5% GLC where $[\alpha]020 = +49$ (c 1, methanol).

EXAMPLE 6

A test tube of *Cladosporium suaveolens*, grown on MPGA (20 g/l malt extract, 5 g/l peptone, 20 g/l glucose, 15 g/l agar) at 24° C. for seven days, is inoculated into a 300 ml Erlenmeyer flask containing 50 ml of MPGB (20 g/l malt extract, 5 g/l peptone, 20 g/l glucose, made up with water). The flask is placed in a thermostatically controlled chamber at 30° C. and kept agitated for two days.

This pre-inoculum is used to seed 300 ml flasks containing 50 ml MPGB, with 5 ml to each flask.

These flasks are cultured for four days at 30° C. without agitation, at which point the medium is replaced by 100 ml of meat extract (20 g/l), 5 g of ricinoleic acid and 0.2 Tween and agitated at 30° C.

The production of gamma decanolide is monitored by means of successive extractions after two, three, four, five and seven days.

Extraction after four days: weight of crude extract: 3 g, GLC analysis, gamma decanolide 20%, gamma decanolide isolated by distillation: 0.5 g.

Extraction after five days: weight of crude extract: 3 g, GLC: 17%.

Extraction after seven days: weight of crude extract: 3 g, GLC: 17%.

EXAMPLE 7

*Cladosporium suaveolens* from an MPGA test tube grown for two days is inoculated into a 300 ml Erlenmeyer flask containing 100 ml of medium prepared with meat extract (5 g/l) and 0.2% Tween. It is left to grow for two days at 30° C. under agitation.

At this point 1 ml of ricinoleic acid is added, which brings the pH to 6.5. The mixture is agitated at 30° C. for 18 days. 1.1 g of crude extract, which proves to contain 40% gamma decanolide, is obtained from four flasks (equivalent to 5 g of ricinoleic acid).

EXAMPLE 8

An inoculum of *Cladosporium suaveolens* from a test tube is added to a 300 ml Erlenmeyer flask containing a medium comprising meat extract (5 g/l) and 0.2% Tween and 1 g of ricinoleic acid (all sterilized together). After nine days under agitation at 30° C. the pH has become 6.5. The contents of two flasks (corresponding to 2 g of ricinoleic acid) are extracted and 0.33 g of crude extract containing 62% gamma decanolide are obtained.

EXAMPLE 9

The procedure in Example 6 is repeated up to the point at which the medium is replaced with 100 ml of meat extract. At this point 5 g of sunflower oil and 0.2% of Tween are added instead of the ricinoleic acid. The mixture is agitated and then extracted after 15 days: crude extract: 2.6 g; % lactone: GLC 31% (38% after lactonization). This material is distilled at 150° C. and 2 mm Hg to give 0.350 g of pure gamma decanolide.

EXAMPLE 10

A 300 ml Erlenmeyer flask containing 100 ml of nutrient broth (20 g/l), 0.2 g of Tween and 5 g of ricinoleic acid is seeded with a pre-inoculum of *Pichia etchellsii* grown on GYP (50 g/l glucose, 10 g/l yeast extract, 10 g/l peptone) for 24 hours. This pre-inoculum in the flask was inoculated from a test tube on MPGA. The contents of the test tube had been allowed to grow for two days at 24° C. The pH is 6.

The mixture is grown at 30° C. under agitation; after six days two flasks (corresponding to 10 g of ricinoleic acid) are extracted. The crude extract weighs 7 g and contains 3.8% of gamma decanolide.

After seven days two flasks are extracted, corresponding to 10 g of ricinoleic acid, to give a crude extract which is distilled in a balloon flask. 0.18 g of gamma decanolide are obtained.

After nine days four flasks are extracted, corresponding to 20 g of ricinoleic acid. The crude extract weighs 4.4 g. 2.2 g of this material are distilled in a balloon flask to give 0.1 g of gama decanolide (43%) whilst before distillation the crude extract contained 4.4% gamma decanolide.

Four flasks are extracted after 15 days. The crude extract is taken up with hexane and then extracted with 1:1 methanol/5% K2C03. The hexane phase is concentrated to give approx. one g of material containing 12% lactone.

EXAMPLE 11

A 300 ml Erlenmeyer flask containing 100 ml of medium based on meat extract (20 g/l), 0.2 g of Tween and 2 g of ricinoleic acid (all sterilized together) is inoculated with *Pichia etchellsii* 5.10 8 cells/ml from a preculture (example 10).

After five days under agitation at 30° C., one flask corresponding to 2 g of ricinoleic acid is acidified to pH 3 and heated at 100° C.

Distillation is continued during 2 hours and the water condensate is extracted with hexane to give 0.2 g of R$\gamma$-decanolide.

EXAMPLE 12

A 300 ml Erlenmeyer flask containing 100 ml of medium comprising meat extract (5 g/l), 0.2% Tween and 1 g of ricinoleic acid (all sterilized together) is inoculated with *Pichia etchellsii* direct from a test tube.

Two flasks corresponding to 2 g of ricinoleic acid are extracted after two days. The crude extract weighs 0.32 g and contains 23% of gamma decalactone.

Two further flasks are extracted after five days. Crude extract 0.36 g, 5.3% gamma decanolide.

EXAMPLE 13

A 300 ml Erlenmeyer flask containing 100 ml of medium comprising meat extract (5 g/l), 0.2% Tween and 1 g of coconut oil (shown to be free from gamma octanolide) is inoculated with *Cladosporium suaveolens* direct from a test tube. Extraction is carried out after five days and produces approx. 100 mg of gamma-octanolide.

We claim:

1. A process for the production of an optically active gamma-lactone selected from gamma-decalactone and gamma-octalactone comprising contacting a vegetable oil or a hydrolysate thereof or ricinoleic acid with a growing culture of a microorganism selected from the group consisting of *Cladosporium suaveolens, Phanerochaete chrysosporium,* and *Pichia etchellsii,* at a pH and temperature and for a time period sufficient for said microorganism to produce said gamma-lactone.

2. A process for the production of an optically active gamma-octalactone comprising contacting a vegetable oil selected from the group consisting of sunflower oil and coconut oil, or a hydrolysate thereof with a growing culture of a microorganism selected from the group consisting of *Aspergillus niger, Cladosporium suaveolens, Phanerochaete chrysosporium,* and *Pichia etchellsii,* at a pH and temperature and for a time period sufficient for said microorganism to produce said gamma-octalactone.

3. The process according to claim 1 or claim 2, wherein said pH is about 5 to about 7, temperature is about 20 degrees to about 30 degrees C. and said reaction time is about 24 to about 60 hours.

4. Process according to claim 1 in which the vegetable oil is selected from castor oil, sunflower oil and coconut oil.

5. Process according to claim 1, in which *Cladosporium suaveolens* and coconut oil are used to produce gamma octanolide.

6. Process according to claim 1 or claim 2 in which the vegetable oil is hydrolysed enzymatically by lipase.

7. Process according to claim 1 in which the gamma hydroxy decanoic acid is lactonized by the action of heat at acid pH.

8. Process according to claim 1 or 7 in which the R γ-decalactone is stripped by water vapor from the acidified medium.

* * * * *